(12) United States Patent
Shaish et al.

(10) Patent No.: US 9,180,152 B2
(45) Date of Patent: Nov. 10, 2015

(54) METHOD FOR TREATING PSORIASIS

(75) Inventors: Aviv Shaish, Talmei Yehyel (IL); Dror Harats, Ramat Gan (IL); Shoshana Greenberger, Newton, MA (US)

(73) Assignees: NIKKEN SOHONSHA CORPORATION, Hashima, Gifu (JP); TEL HASHOMER MEDICAL RESEARCH INFRASTRUCTURE AND SERVICES LTD., Tel Hashomer (IL)

( * ) Notice: Subject to any disclaimer, the term of this patent is extended or adjusted under 35 U.S.C. 154(b) by 0 days.

(21) Appl. No.: 13/512,416

(22) PCT Filed: Dec. 5, 2010

(86) PCT No.: PCT/IL2010/001026
§ 371 (c)(1),
(2), (4) Date: May 29, 2012

(87) PCT Pub. No.: WO2011/070568
PCT Pub. Date: Jun. 16, 2011

(65) Prior Publication Data
US 2012/0237597 A1    Sep. 20, 2012

Related U.S. Application Data

(60) Provisional application No. 61/285,358, filed on Dec. 10, 2009.

(51) Int. Cl.
*A61K 36/05* (2006.01)
*A61K 36/02* (2006.01)

(52) U.S. Cl.
CPC ..................................... *A61K 36/05* (2013.01)

(58) Field of Classification Search
None
See application file for complete search history.

(56) References Cited

U.S. PATENT DOCUMENTS

| | | | |
|---|---|---|---|
| 4,642,318 A | 2/1987 | Wolff | |
| 5,034,228 A | 7/1991 | Meybeck et al. | |
| 6,248,340 B1 | 6/2001 | Maor et al. | |
| 7,264,813 B2 | 9/2007 | Shaish et al. | |
| 8,529,907 B2 | 9/2013 | Belkin et al. | |
| 2003/0159221 A1 | 8/2003 | Lang | |
| 2008/0206377 A1* | 8/2008 | Scott .............................. | 424/777 |
| 2009/0169586 A1 | 7/2009 | Tracton | |
| 2009/0324705 A1 | 12/2009 | Vikhrieva | |
| 2011/0045035 A1 | 2/2011 | Belkin et al. | |
| 2014/0023702 A1 | 1/2014 | Belkin et al. | |

FOREIGN PATENT DOCUMENTS

| | | | |
|---|---|---|---|
| CH | 685325 | A5 | 6/1995 |
| FR | 2805741 | A1 | 9/2001 |
| FR | 2805742 | A1 | 9/2001 |
| JP | 9110669 | | 4/1997 |
| JP | 9110669 | A | 4/1997 |
| JP | 11228437 | A | 8/1999 |
| JP | 2008543757 | | 12/2008 |
| JP | 2011518875 | | 6/2011 |
| WO | 9518605 | | 7/1995 |
| WO | 9902128 | | 1/1999 |
| WO | 2006135635 | | 12/2006 |
| WO | 2006135635 | A2 | 12/2006 |
| WO | 2007109824 | A1 | 10/2007 |
| WO | WO2007109824 | A1 * | 10/2007 |
| WO | 2009133552 | | 11/2009 |
| WO | 2009133552 | A2 | 11/2009 |

OTHER PUBLICATIONS

Bollag, W. et al, "Successful Treatment of Chronic Hand Eczema with Oral 9-cis-Retinoic Acid", Dermatology, 1999, 199:308-312, S.Karger AG, Basel, Oberrieden, Switzerland.
Peter C.M. Van De Kerkhof, "Update on retinoid therapy of psoriasis in: an update on the use of retinoids in dermatology", Dermatologic Therapy, 2006, 252-263, Blackwell Publishing, Inc. USA.
Sheba Medical Center, "The Effect of Algae Dunaliella Bardawil on Psoriasis (2)", Clinical Trials, 2010, Ramat Gan, Israel (XP002629512).
Saurat, J.-H, "Topical Natural Retinoids", Dermatology, 1999, 199;1-2, S.Karger AG, Basel, Geneva, Switzerland.
MacDonald, K. "Is There a Place for B-Carotene/Canthaxanthin in Photochemotherapy for Psoriasis?", Dermatologica, 1984, 169:41-46, S.Karger AG, Basel, Dundee, United Kingdom.
Basilea Pharmaceutica, Toctino information sheet, 2008, United Kingdom.
International Preliminary Report on Patentability (IPRP) published Jun. 12, 2012 for International Patent Application No. PCT/IL2010/001026.
Written Opinion (WO) published Jun. 10, 2012 for International Patent Application No. PCT/IL2010/001026.
International Search Report (ISR) published Jun. 16, 2012 for International Patent Application No. PCT/IL2010/001026.
European Office Action dated Mar. 31, 2014 for Application No. 10 798833.9-1456.
Exhibit A, "Retinoids and Carotenoids in Dermatology", edited by Vahlquist et al, pp. 134, 2007 by Informa Healthcare USA, Inc.
Exhibit B, "Background for Advisory Committee Meeting to Discuss Oral Tazarotene for the Treatment of Moderate to Severe Psoriasis" pp. 1-27 by US FDA, 2003.
Exhibit C, "Generalized pustular psoriasis induced by systemic glucocorticosteroids: four cases and recommendations or treatment", Brenner et al, pp. 964-970, 2009, British Journal of Dermatology, 161.
Yutaka Nakaya and Susumu Ito; "Vitamin preparation-required clinical conditions and administration methods;" The Japanese Journal of Clinical and Experimental Medicine, vol. 73 No. 10 pp. 2,218 to 2,222 (1996).

(Continued)

*Primary Examiner* — Chris R Tate
*Assistant Examiner* — Randall Winston
(74) *Attorney, Agent, or Firm* — Fleit Gibbons Gutman Bongini & Bianco PL; Martin Fleit; Paul D. Bianco

(57) ABSTRACT

The invention is a method for treating psoriasis in a subject suffering from psoriasis. The method includes orally administering to the subject a pharmaceutically-effective amount of crude *Dunaliella* powder.

3 Claims, 2 Drawing Sheets

(56) References Cited

OTHER PUBLICATIONS

English translation of Yutaka Nakaya and Susumu Ito; "Vitamin preparation-required clinical conditions and administration methods;" The Japanese Journal of Clinical and Experimental Medicine, vol. 73 No. 10 pp. 2,218 to 2,222 (1996).

Japanese Office Action drafted Oct. 23, 2013 for Application No. 2012-542685.

English translation of Japanese Office Action drafted Oct. 23, 2013 for Application No. 2012-542685.

Keeichi Watanabe et al.; "Cis-Trans Isomers of β-Carotene in Fresh Vegetables and Fruits;" Food Sci Technol Res., vol. 5 No. 3 pp. 308 to 310 (1999).

Office Action dated May 13, 2015 for Israeli Application No. 220083 (with Eng translation).

\* cited by examiner

| Treatment | PASI 50% | PASI 75% |
|---|---|---|
| Control | 45% | 27% |
| Dunaliella | 80% | 40% |

METHOD FOR TREATING PSORIASIS

FIELD OF THE INVENTION

This invention relates to a method for treating psoriasis.

BACKGROUND OF THE INVENTION

Psoriasis is a chronic skin disease affecting approximately 2-3% of the world population. Presently, psoriasis is without a permanent cure and its influence on the affected individual's life quality is devastating. People often experience flares and remissions throughout their life. Although new biological-immunological therapies are being developed, the mainstay armamentarium to treat psoriasis systemically includes methotrexate, cyclosporin and oral retinoids. Each treatment has advantages and disadvantages, and what works for one patient may not be effective for another.

Since the 1930s, vitamin A deficiency has been known to cause hyperkeratosis of the skin (phrynoderma) and as early as 1960s synthetic Vitamin A has been used for the treatment of psoriasis, though with low efficacy over toxicity ratio. Further research resulted in the development of the second generation of retinoids, the mono-aromatic retinoids, etretinate and its metabolite acitretin. Etretinate and acitretin are highly effective systemic treatments for psoriasis as well as for disorders of keratinization and for cutaneous lupus. However, despite the demonstrated clinical success of retinoid therapy, this treatment has a significant potential for toxicity, especially elevated liver functions and elevated triglycerides and LDL-Cholesterol and it requires close laboratory supervision. In addition, teratogenicity, the primary side-effect of retinoids, remains a major concern.

There are several forms of psoriasis, and each form has unique characteristics that allow dermatologists to visually identify psoriasis to determine what type, or types, of psoriasis is present. Sometimes a skin biopsy will be performed to confirm the diagnosis. The main types of psoriasis include the following:

Plaque Psoriasis (reddened areas a few inches across covered by silvery scales)
Pustular Psoriasis (blisters of noninfectious pus on red skin)
Arthritic Psoriasis or Psoriatic Arthritis
Guttate Psoriasis (small, red spots on the skin)
Inverse or Flexural Psoriasis (shiny, red patches in areas of friction such as in the folds of skin in the groin, the armpits or under the breasts)
Erythrodermic Psoriasis (reddening and scaling of most of the skin).

Treatment depends on the severity and type of psoriasis. Some psoriasis is so mild that the person is unaware of the condition. A few develop such severe psoriasis that lesions cover most of the body and hospitalization is required. These represent the extremes. Most cases of psoriasis fall somewhere in between.

Psoriasis treatments fall into 3 categories:
Topical (applied to the skin)—Mild to moderate psoriasis
Phototherapy (light, usually ultraviolet, applied to the skin)—Moderate to severe psoriasis
Systemic (taken orally or by injection or infusion)—Moderate, severe or disabling psoriasis.

Bollag, W. and Ott, F. (1999) Dermatology 199:308-312, describe the treatment of chronic hand eczema with oral 9-cis-retinoic acid. The article states that "Psoriasis . . . did not respond to well-tolerated doses of oral 9-cis-retinoic acid".

Peter C. M. van de Kerkhof (2006) Dermatologic Therapy 19:252-263, describes the use of Acitretin (SORIATANE®, Roche Pharmaceuticals), a second generation oral systemic retinoid, for the treatment of psoriasis.

SUMMARY OF THE INVENTION

In a first aspect, the present invention relates to a method for treating psoriasis in a subject comprising orally administering to the subject a pharmaceutically effective amount of crude *Dunaliella* powder.

The active ingredient in accordance with the invention is a substantially crude *Dunaliella* algae preparation, typically dried *Dunaliella* algae. The term "crude" comes to exclude an extract or purified compound obtained from *Dunaliella* algae. The *Dunaliella* algae are preferably *Dunaliella bardawil*. Other species include *D. salina, D. viridis, D. peircei, D. parva, D. media, D. euchlora, D. minuta, D. tertiolecta, D. primolecta, D. acidophila, D. quartolecta* and *D. polymorpha*.

In a preferred embodiment, the substantially crude *Dunaliella* algae preparation contains β-carotene (BC) at an approximately 1:1 ratio of 9-cis to all-trans isomers of BC or greater than 1:1 ratio of 9-cis to all-trans isomers of BC.

The terms "treating" or "treatment" in the present specification should be understood as bringing about an improvement in the pathological symptoms of the disease, and in some cases curing the disease. The effectiveness of a psoriasis therapeutic treatment of a subject may be assessed at various time points before, during and after the treatment by one or more of the following: Psoriasis Area and Severity Index (PAST); Percentage (%) of skin covered with psoriasis; Dermatology Life Quality Index (DLQI); Patient Global Assessment of Psoriasis Activity and Physician Psoriasis Global Assessment (PGA). The severity of the disease may be determined by various conventional methods such as by pathological techniques.

An "effective amount" should be understood as an amount or dose of the active ingredient which is sufficient to achieve the desired therapeutic effect, i.e. treatment of the indicated diseases. The effective amount depends on various factors including the severity of the disease, the administration regimen, e.g. whether the preparation is given once or several times over a period of time, the physical condition of the subject; etc. The artisan should have no difficulties, by minimal experiments, to determine the effective amount in each case. In one embodiment of the invention, the expected dose range may be 1-6 capsules per day, 300 mg *Dunaliella* powder per capsule.

The crude *Dunaliella* powder is preferably administered orally, for example in an encapsulated form. However, other systemic, non-topical forms of administration are contemplated such as *Dunaliella* powder formulated with pharmaceutically-acceptable excipients for intravenous, intramuscular, intraperitoneal or subcutaneous administration.

In a second aspect of the invention, there is provided a pharmaceutical composition for treating psoriasis in a subject comprising crude *Dunaliella* powder.

In a third aspect of the invention, there is provided a use of a pharmaceutically effective amount of crude *Dunaliella* powder for the preparation of a pharmaceutical composition for treating psoriasis in a subject.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figures 1, 2:
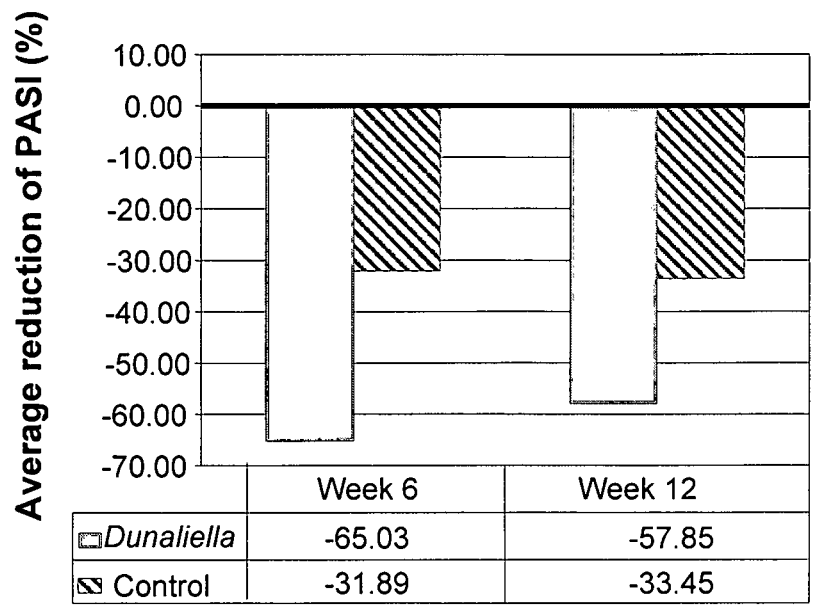
FIG. 1 is a bar graph showing average Psoriasis Area and Severity Index (PAST) reduction in *Dunaliella*-treated and control groups after 6 and 12 weeks of treatment.
FIG. 2 is a table showing the % of patients who reached PASI 50% and PASI 75% after 12 weeks in the *Dunaliella*-treated and control groups.

All of the human studies described below employed capsules containing *Dunaliella* powder prepared as follows.

*Dunaliella bardawil* (hereinafter "Db") was grown and cultivated in large body open salt water ponds of 50,000 $m^2$ to obtain algae comprising approximately 8% by weight of β-carotene (hereinafter "BC") at an approximately 1:1 (by weight) ratio of 9-cis and all-trans isomers of BC, or greater than 1:1 ratio of 9-cis and all-trans isomers of BC. The algae were harvested by dislodging centrifuges into a concentrated paste. The paste was washed to remove the salt and sterilized, and then spray dried to yield Db powder comprising approximately 8% BC and less than 5% moisture. The powder was packaged in capsules of 250-300 mg algae containing 15-20 mg of BC each together with all of the natural components of the algae. The BC of the capsules retains the original ratio of isomers. The capsules are packaged in vacuum closed blisters which have a shelf life of up to three years.

EXAMPLE I

Patients and Methods

The study was randomized, double-blind, and vehicle-controlled. Eligible patients were 18 years of age or older with stable, active plaque psoriasis involving 10% body surface area (BSA) or less. Exclusion criteria were: serious or unstable medical or psychological condition, active liver or renal disease, smoking, history of alcohol or drug abuse within the past one year, pregnancy, or planning on becoming pregnant. Concomitant topical therapy, phototherapy or systemic therapy for psoriasis was prohibited throughout the study, with the exception of emollients. Patients, investigators, and all study staff were blinded to treatment assignments.

Patients were randomly assigned into two groups: 22 subjects were treated with *Dunaliella* capsules and 11 subjects (control) were treated with capsules containing starch powder, as the placebo. Treatment dosage was four capsules of the alga *D. bardawil* (Nikken Sohonsha Corporation, Gifu, Japan), two capsules after breakfast and two after dinner. Each capsule contained 15-20 mg β-carotene with a ratio of 9-cis β-carotene to all-trans β-carotene of about 1:1.

An institutional review board or ethics committee approved the study protocol. Written informed consent was obtained from patients before the start of any study related procedure.

Clinical Efficacy Evaluation

As a measure of the clinical response, (Psoriasis Area and Severity Index) PASI scores were given by an investigator blinded to the treatment assignment at baseline, after 6 weeks and at completion of the study (12 weeks). As a marker of inflammation, the acute phase protein C-reactive protein (CRP) was measured using a commercial kit by autoanalyzer (Olympus). Digital photographing of the lesions was carried out by the same schedule. A Dermatology Life Quality Index (DLQI) questionnaire was used to evaluate the quality of life of patients at 0, 6 and 12 weeks.

Safety and Tolerability Evaluation

At the pre-study visit, the medical history was recorded and a physical examination, including vital parameters (e.g. blood pressure, pulse, weight, and temperature), was completed. A blood sample was taken for analysis of complete blood cell counts, liver and renal functions, fasting lipid analysis, 9-cis β-carotene, and all-trans β-carotene at baseline and at 6 and 12 weeks.

Nutritional Evaluation

Patients' dietary intakes were assessed by the 24 h recall method delivered by an experienced nurse, directed by a clinical dietitian, on 3 days during the 12 week period, 2 days in the middle of the week and 1 day on the weekend. The data was analyzed for nutrient content by the nutrition data system of the International Center of Health and Nutrition at Ben-Gurion University, Beer-Sheba, Israel.

Statistical Analysis

Paired t-test or Wilkoxon signed ranked test for non-parametric variables were used to compare the results of the human group before and after the *Dunaliella* administration. Pearson's correlation test was used to detect the link between variables. Statistical tests were all two-sided. $P<0.05$ was accepted as statistically significant.

Results

Efficacy 33 patients were recruited. 7 patients did not attend treatment sessions regularly or failed to comply with the study requirements and were excluded from evaluation. 26 patients completed the study; of these, 15 had received treatment with *Dunaliella* and 11 with control, placebo pills. The characteristics of the two patient cohorts are given in Table I. The treatment groups were similar in demographic and disease characteristics at baseline. All participants who completed the trial were at least 85% compliant with the treatment regimen as determined by patient interview and pill counts. The results are summarized in FIGS. 1 and 2.

TABLE 1

Characteristics of the two patient cohorts.

|  | *Dunaliella* | Control |
|---|---|---|
| Age (median, IQR) | 52 (39-56) | 52 (39-65) |
| Males | 9 | 8 |
| Females | 6 | 3 |
| Weight | 76 | 81 |
| Systolic blood pressure | 121 | 130 |
| Diastolic blood pressure | 80 | 86 |
| pulse | 72 | 71 |
| fasting glucose | 91 | 93 |
| blood creatinin | 1 | 1 |
| Total cholesterol | 185 | 209 |
| TG | 97 | 139 |
| HDL | 49 | 48 |

Figure 3:
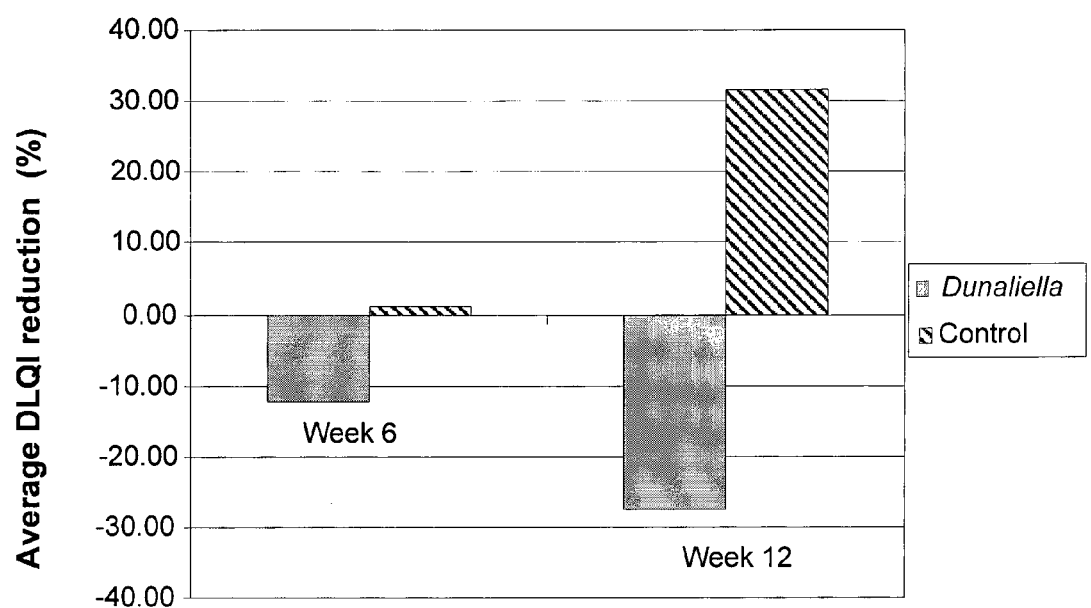
FIG. 3 is a bar graph showing average Dermatology Life Quality Index (DLQI) reduction in *Dunaliella*-treated and control groups after 6 and 12 weeks of treatment.

After six weeks of twice-daily treatment, PASI scores were significantly reduced from baseline in patient group treated with *Dunaliella*, whereas the control group did not reach significance (P=0.04 vs. P=0.6, respectively). Similar results were obtained after 12 weeks of treatment (P=0.004 vs. P=0.07, respectively). The number of patients reached PASI 50% after 12 weeks of treatment was 80% in *Dunaliella* group and 45% in control group. The number of patients reached PASI 75% after 12 weeks of treatment was 40% in *Dunaliella* group and 27% in control group. In order to evaluate *Dunaliella* effect on the patient's quality of life, DLQI assay was performed. The results are summarized in FIG. 3. The mean change from baseline to week 6 and 12 was 12 and 27.6 (P=0.009 for 12 weeks) in the *Dunaliella* group, respectively. In the control group the mean change was 5.9 and −21.9 (P=0.93 for 12 weeks), respectively.

As a surrogate marker for inflammation, CRP levels were analyzed at the baseline and at weeks 6 and 12. Significant reduction in CRP was found in the *Dunaliella* group but not in the control group.

Thus, the treatment with *Dunaliella* resulted in a significant improvement in the psoriasis patients.

Safety

There were no treatment-related adverse events in the overall study. In the *Dunaliella* group, one patient had a myocardial infarction during percutanerous transluminal coronary angioplasty leading to an emergency coronary artery bypass. In the control group, one patient had syncope, without a known cause. Two patients in the *Dunaliella* group reported accelerated hair growth and darkening of hair.

The invention claimed is:

1. A method for treating plaque psoriasis in a subject in need thereof comprising orally administering to the subject a pharmaceutically effective amount of crude *Dunaliella* powder, wherein the *Dunaliella* powder comprises 9-cis β-carotene to all-trans isomers of β-carotene (BC) having a weight ratio of at least 1:1, respectively.

2. The method of claim 1, wherein the *Dunaliella* powder is encapsulated.

3. The method claim 1, wherein the *Dunaliella* is selected from the group consisting of *Dunaliella bardawil, D. salina, D. viridis, D. peircei, D. parva, D. media, D. euchlora, D. minuta, D. tertiolecta, D. primolecta, D. acidophila, D. quartolecta* and *D. polymorpha*.

* * * * *